(12) United States Patent
Shechtman et al.

(10) Patent No.: US 10,898,623 B2
(45) Date of Patent: *Jan. 26, 2021

(54) DEVICE FOR PREVENTION OF SHUNT STENOSIS

(71) Applicants: TECHNION RESEARCH & DEVELOPMENT FOUNDATION LTD., Haifa (IL); MICROBOT MEDICAL LTD, Yokneam (IL)

(72) Inventors: Adi Shechtman, Nofit (IL); Moshe Shoham, Hoshaya (IL); Harel Gadot, New York, NY (US)

(73) Assignee: MICROBOT MEDICAL LTD., Yokneam (IL)

( * ) Notice: Subject to any disclaimer, the term of this patent is extended or adjusted under 35 U.S.C. 154(b) by 874 days.

This patent is subject to a terminal disclaimer.

(21) Appl. No.: 15/592,227

(22) Filed: May 11, 2017

(65) Prior Publication Data
US 2017/0239401 A1      Aug. 24, 2017

Related U.S. Application Data

(63) Continuation of application No. 14/348,610, filed as application No. PCT/IL2012/000352 on Sep. 27, 2012, now Pat. No. 9,675,748.
(Continued)

(51) Int. Cl.
*A61M 1/36*     (2006.01)
*A61M 1/00*     (2006.01)
(Continued)

(52) U.S. Cl.
CPC ... *A61M 1/0078* (2013.01); *A61B 17/320725* (2013.01); *A61M 1/367* (2013.01);
(Continued)

(58) Field of Classification Search
CPC .............. A61M 1/0078; A61M 1/3655; A61M 2025/1072; A61M 2025/109;
(Continued)

(56) References Cited

U.S. PATENT DOCUMENTS

| 4,016,879 A | 4/1977 | Mellor |
| 6,454,775 B1 | 9/2002 | Demarais et al. |

(Continued)

FOREIGN PATENT DOCUMENTS

| EP | 0330376 A2 | 8/1989 |
| WO | WO 01/97697 A1 | 12/2001 |

(Continued)

OTHER PUBLICATIONS

PCT International Search Report and Written Opinion of the ISA, dated Jan. 29, 2013 in PCT/IL2012/000352.
(Continued)

*Primary Examiner* — Kai H Weng
(74) *Attorney, Agent, or Firm* — Daniel Feigelson

(57) ABSTRACT

A method and a kit for the prevention of venous stenosis associated with the use of hemodialysis AV shunts. The kit may use a bifurcated needle for providing access to the shunt or blood vessel. One of the arms is used for returning the blood to the subject after dialysis treatment, while the other arm is used for inserting a device for cleaning the vein, the device being either an autonomous crawling device, or a passive tethered device moved down the vein by the blood flow. The autonomous crawling device may be a series of sequentially inflatable chambers, the stenosis being cleared by pressure from the outer walls of the chambers when inflated and moved. The passive device may be an element having a flexible disc-like structure, whose flexible peripheral edge slides along the inner walls of the blood vessel, compressing or clearing the material attached thereto.

20 Claims, 4 Drawing Sheets

Related U.S. Application Data

(60) Provisional application No. 61/626,586, filed on Sep. 29, 2011.

(51) Int. Cl.
  *A61M 25/01* (2006.01)
  *A61B 17/3207* (2006.01)
  *A61M 25/10* (2013.01)

(52) U.S. Cl.
  CPC ...... *A61M 1/3655* (2013.01); *A61M 25/0116* (2013.01); *A61M 25/0155* (2013.01); *A61M 25/1011* (2013.01); *A61M 25/104* (2013.01); *A61M 2025/109* (2013.01); *A61M 2025/1072* (2013.01); *A61M 2025/1097* (2013.01); *A61M 2209/10* (2013.01)

(58) Field of Classification Search
  CPC ...... A61M 2025/1097; A61M 2209/10; A61M 25/0116; A61M 25/0155; A61M 25/1011; A61M 25/104
  See application file for complete search history.

(56) References Cited

U.S. PATENT DOCUMENTS

| | | |
|---|---|---|
| 2007/0038244 A1 | 2/2007 | Morris et al. |
| 2007/0142770 A1* | 6/2007 | Rioux ................... A61M 25/10 604/93.01 |
| 2008/0108930 A1 | 5/2008 | Weitzel |
| 2008/0249461 A1 | 10/2008 | Foreman et al. |
| 2011/0125132 A1 | 5/2011 | Krolik et al. |

FOREIGN PATENT DOCUMENTS

| | | |
|---|---|---|
| WO | WO 2007/017876 A2 | 2/2007 |
| WO | WO 2007/102909 A2 | 9/2007 |
| WO | WO 2008/051431 A1 | 5/2008 |
| WO | WO 2008/099389 A2 | 8/2008 |
| WO | WO 2010/017537 A2 | 2/2010 |

OTHER PUBLICATIONS

European Extended Supplementary Search Report in corresponding European patent application No. 12837337.0 dated Nov. 6, 2015.

* cited by examiner

DEVICE FOR PREVENTION OF SHUNT STENOSIS

RELATED APPLICATIONS

This application is a continuation of U.S. Ser. No. 14/348, 610, which is the national stage of PCT/IL2012/000352, filed Sep. 27, 2012, which claims the benefit of U.S. Ser. No. 61/626,4586, filed Sep. 29, 2011. The contents of these applications are incorporated herein by reference.

FIELD OF THE INVENTION

The present invention relates to the field of devices and methods for use in the prevention of stenosis in blood vessels, especially for use on blood vessels adjacent to a hemodialysis shunt.

BACKGROUND OF THE INVENTION

The extraction of blood for hemodialysis is generally performed on a vein. However, the flow of blood in the veins, coming from the capillaries, is generally too slow for the flow required for efficient hemodialysis. In order to ensure a sufficiently fast flow of blood in the vein, a procedure is used to join an adjacent artery to the vein, allowing arterial blood to flow directly into the vein, thereby boosting its flow rate. A commonly used site is a blood vessel of the arm, e.g. at the wrist or at the upper forearm. Due to the arterial pressure, the vein should increase in size and its walls thicken, such that it is then easier to put needles into this vein to extract and to return the blood. The arterial-venous (AV) join is generally performed either directly, to produce an AV fistula, or by means of a surgically inserted artificial AV graft or shunt joining artery and vein. Shunts are inserted when the patient's native vasculature does not permit a fistula. The shunt, which may be either straight or looped, is close to the surface of the skin for easier needle insertion. The shunt may be constructed of an artificial material such as polytetrafluoroethylene or Gor-tex®, or can be obtained from the patient's own body such as a vein in the thigh, or from a specially treated animal blood vessel. The use of an AV shunt enables the needle access to be made in the shunt, rather than in the patient's own vein, though either procedure may be used.

However, such shunts, both of the fistula and AV type, have a problem in that they are often associated with stenosis of the vein into which they are inserted, usually just downstream from the point where the shunt has been sewn into the vein, or the point where the artery and vein are sewn together. Such venous narrowing often leads to clotting or thrombosis, and if untreated, could lead to complete blockage of the vein, often within less than a year of the insertion of the shunt. The cause for this phenomenon is unknown, but it is thought that it may be associated with the turbulent flow of the blood in that region of the vein. This stenosis has traditionally been treated by means of balloon angioplasty performed in the region downstream of the shunt. However, this procedure is costly, involving complex instrumentation and x-ray surveillance generally available only in the hospital environment, generally has to be repeated at intervals of several months, and has the associated dangers of venous rupture if excess pressure is applied.

There therefore exists a need for an apparatus and method for preventing venous stenosis associated with the use of AV shunts, which overcomes at least some of the disadvantages of prior art systems and methods.

The disclosures of each of the publications mentioned in this section and in other sections of the specification, are hereby incorporated by reference, each in its entirety.

SUMMARY

The present disclosure describes a new exemplary method and a kit or system for the prevention of venous stenosis associated with the use of hemodialysis AV shunts. The kit is simple in construction and simple in operation such that it can be used by auxiliary medical personnel, or even by the patient him/herself in the home setting, if dialysis is performed there. The kit may use a bifurcated needle, such as a Y-needle, for providing access to the shunt or blood vessel. The blood is generally drawn from the patient for transfer to the dialysis machine through a needle upstream of the Y-needle, and of the two arms of the Y-needle, one is used for returning the blood to the shunt or vein after treatment in the dialysis apparatus, while the other arm is used for inserting a device for cleaning the vein, the device being either an autonomous crawling device, or a passive tethered device moved down the vein by the blood flow. Thus, while the device is being inserted into one arm of the Y-needle, the dialysis can continue through the other arm while the cleaning process is performed. This Y-needle can be inserted either into the shunt itself or into the vein immediately below the point at which the shunt is joined to the vein. Insertion of the device into the same lumen with the returning blood flow is advantageous, since the stenosis generally occurs in the vein after the junction point with the shunt, where the blood flows back into the vein.

One such convenient autonomous crawling device is the self-propelled device for locomotion through a lumen described in the PCT patent application, International Publication No. WO 2007-017876, for "Tip Propelled Device for Motion through a Passage". This device uses a series of sequentially inflatable chambers to make up the traction unit, such that the chamber or chambers at the rear or proximal end of the series grips the inside wall of the blood vessel, while the device expands forward with inflation of the other chambers, and then the chamber or chambers situated at the front or distal end of the series grips the inside wall of the blood vessel while the device pulls up its rear end with deflation of the other chambers. By use of suitably dimensioned apertures between chambers, this sequential inflation/deflation procedure can be accomplished using only a single fluid inflation tube attached to the rear or proximal chamber. Such a device may have overall diametric size sufficiently small that it can be inserted through the comparatively small bore of the Y-needle before inflation, but on inflation, its outer diameter becomes such as to reach and obtain a grip on the inner wall of the blood vessel.

As the chambers inflate against the inner wall of the blood vessel through which it is passing, any undesired stenosis tissue or plaque within the blood vessel will be compressed against the wall, thus maintaining the blood vessel clear of obstruction. Once the device has traversed the sections of the vein which require removal of the blocking material, or prevention of the growth thereof, the device can be pulled back out by means of the flexible inflation tube attached to its rear or proximal end, deflated, and removed from the patient. Alternatively, the device may be allowed to traverse the section to be treated several times, to and fro, by pulling the device back by means of its inflation tube, and then allowing it to crawl forward again. One other alternative is to push the device forward by means of a guide wire, in a similar manner as is done in coronary angioplasty.

However, it should be emphasized that despite certain superficial similarity of some aspects of the implementations in this disclosure with balloon angioplasty, there is a significant difference between the present application and balloon angioplasty. With balloon angioplasty, the treatment is carried out under X-ray surveillance, in order that the balloon be positioned and the treatment performed at the exact location of the blockage or near blockage, The present system, on the other hand, has no need for any external surveillance system or methods, and the device for clearing or preventing stenosis growth is simply inserted into the vein, and is allowed to roam freely to and fro if necessary along any section of the vein which the length of the paid-out tether allows the device to reach.

The chambers of the device may be constructed to enable continued flow of blood past the device when it is traversing the blood vessel, such as in the form of less elastic sections of the outer walls of the chambers, such that those sections do not inflate to reach the blood vessel inner wall, but leave a passage for blood flow, Sequential chambers should then have these lesser inflating sections disposed at different angular positions around the circumference of the chambers, such that no part of the inside wall of the blood vessel is left untreated by the expanding balloons pressing on the inner wall. As an alternative, annular inflatable chambers can be used, these having a central hollow passageway along their axis, allowing the blood to flow therealong. In general, since the flow rate which needs to be maintained past the device need be no more than the dialysis flow rate which is limited by the Y-needle bore, which may be only 1 to 1.5 mm, the cross section needed for free flow of blood past the device may be only a fraction of the total cross section of the blood vessel, which may have a diameter of 3 to 5 mm. However, it is feasible that since the time taken to perform the cleaning procedure is very short, possibly of the order of only tens of seconds, the provision of blood flow relief passages may not be essential since such a short period without significant blood flow in that vein would not be detrimental to the patient or the dialysis procedure. Because of the short time taken to perform the procedure, another advantage is that the procedure can be repeated several times during the dialysis treatment, which can take several hours.

The device may also be provided with a tapered tip which, as the device advances through the passageway, is able to force its way through partial blockages encountered in the blood vessel. The tip partially compresses the blockage material against the wall of the passageway, such that the inflating chambers following can complete the process of opening the blood vessel by means of the radial compression forces. Specific chambers can be constructed in an elongated form, such that when inflated, they apply pressure to a long section of the inner wall of the blood vessel, thereby compressing any growth of stenosis tissue onto the wall over a significant length of the blood vessel.

As an alternative to an active crawling device, it is also possible to use a tethered passive clearing device, such as an inflatable chamber whose outer surface reaches the blood vessel walls when it is inflated, or an element having a flexible disc-like structure, whose flexible peripheral edge can slide along the inner walls of the blood vessel, compressing or clearing the material attached thereto. Such a device can then traverse the blood vessel under the influence of the blood flow itself, clearing the blood vessel as it moves in the stream. Additionally, clearing can also be performed as the device is pulled back in the blood vessel by means of its tether, especially for the flexible disc structure if its peripheral edges are appropriately shaped and constructed, such as to slide along the inside walls of the blood vessel smoothly without danger of injuring it or puncturing it.

Since the use of the stenosis clearing device is so simple, it can be performed at frequent intervals, such as once a month or once a week, or even at every dialysis session. This has the substantial advantage over prior art methods of clearing stenosis, in that it does so at such an early stage of the stenosis, that clearing the unwanted material or prevention of the growth of such unwanted tissue becomes a minor procedure. The likelihood of emboli which could cause a thrombosis is therefore substantially reduced.

Although the kit and method have been described throughout this disclosure using one arm of a Y-needle for inserting the stenosis cleaning device, in parallel with the returned blood flow to the vein through the other arm of the Y-needle, it is to be understood that this arrangement is only described as being a simple configuration for the technique described, and is not intended to limit the invention. Thus, it is also possible to use separate needles for inserting the cleaning device and for returning the blood to the vein, although this entails an additional puncture of the shunt or vein. Furthermore, although the Y-needle, when used, is shown inserted into the shunt itself, it is also feasible to use a single needle puncture, and to have a Y-junction upstream of the connection to that single needle, thus providing the same effect as direct puncture entry of a Y-needle.

One exemplary implementation involves a system for reducing dialysis shunt stenosis in a blood vessel of a subject, the system comprising:

(i) a deployable clearing device, adapted to move down the blood vessel, and (ii) a needle for insertion of the clearing device into the blood vessel of the subject, wherein the clearing device comprises:

(a) at least one cleaning element having a periphery of such a diameter that it contacts the walls of the blood vessel when deployed, the periphery further being adapted to contact the walls of the blood vessel as it moves therealong, and (b) a tether attached proximally to the clearing device for withdrawing the device from the blood vessel, and wherein the clearing device has a stowed diameter sufficiently small that it can pass through the bore of the needle into the blood stream of the subject.

In any such a system, the cleaning element may comprise at least one passage enabling continued flow of blood through the blood vessel when the device is disposed in the blood vessel. Additionally, the deployable blood vessel clearing device may comprise a locomotive system, by means of which the device moves down the blood vessel. Alternatively, the deployable clearing device may comprise at least one element shaped to be swept by the blood flow, such that the device moves down the blood vessel under the influence of the blood flow.

According to other exemplary implementations, the clearing device may comprise at least one inflatable chamber whose inflated diameter is such that its periphery applies pressure to the walls of the blood vessel when the at least one chamber is inflated. In such an implementation, the at least one inflatable chamber may comprise a series of inflatable chambers connected by apertures of a predetermined cross section such that when fluid pressure is applied to the proximal one of the chambers, the chambers sequentially expand radially to the inner wall of the blood vessel and axially along the blood vessel. At least some of the inflatable chambers may then have at least one region at which the outer surface does not touch the inner wall of the blood vessel when the chamber is inflated. These regions may then advantageously be arranged at different angular locations around the periphery of different ones of the chambers In the above described systems, the cleaning element may alternatively comprise at least one flexible disc-shaped element attached to a body, the at least one flexible disc-shaped element having an outer diameter at least as large as the internal diameter of the blood vessel of the subject in the region where the stenosis is expected. In such a case, the clearing device may further comprise threads attached to outer portions of the at least one flexible disc-shaped element, such that the at least one flexible disc-shaped element can be stowed onto the body by means of tension applied to the threads. In either of these instances, at least one of the flexible disc-shaped elements may be constructed of a polymeric material.

Yet other implementations may involve a system as described above, in which the cleaning element is drug eluting, the drug being a stenosis retarding drug.

Additionally, the needle may be either one entry arm of a bifurcated needle, such that the other entry arm is free for flowing blood into the blood vessel, or it may be a single bore needle, the system further comprising a second single bore needle for flowing blood into the blood vessel.

Yet other implementations perform a method of reducing dialysis shunt stenosis in a blood vessel of a subject, the method comprising:

(i) providing a deployable clearing device, and a needle for insertion of the clearing device into the blood vessel of the subject, the clearing device comprising:
  (a) at least one cleaning element having a periphery of such a diameter that it contacts the walls of the blood vessel when deployed and a stowed diameter sufficiently small that it can pass through the bore of the needle, and
  (b) a proximally attached tether;
(ii) inserting the clearing device into the blood vessel through the needle bore, such that it passes down the blood vessel and such that the periphery of the cleaning element contacts the walls of the blood vessel as it moves therealong, and
(iii) withdrawing the device from the blood vessel by means of the tether.

In such a method, the needle may be inserted into the shunt upstream of a junction of the shunt with the blood vessel, or into the blood vessel close to a junction of the shunt with the blood vessel.

Furthermore, in such methods, the deployable clearing device may comprise a locomotive system, the method further comprising the step of using the locomotive system to move the clearing device down the blood vessel. Alternatively, the deployable clearing device may comprise at least one element shaped to be swept by the blood flow, such that the device moves down the blood vessel under the influence of the blood flow.

In any of these methods, the step of withdrawing the device from the blood vessel may be executed after the clearing device has performed at least one passage down the blood vessel, the method further including the step of using the tether to pull back the clearing device proximally after each forward passage.

According to other implementations of these methods, the clearing device may comprise at least one inflatable chamber whose inflated diameter is such that its periphery applies pressure to the walls of the blood vessel when the at least one chamber is inflated. In such a case, the at least one inflatable chamber may comprise a series of inflatable chambers connected by apertures of a predetermined cross section, the method then may comprise the further step of applying fluid pressure to the proximal one of the chambers, such that the chambers sequentially expand radially to the inner wall of the blood vessel and axially along the blood vessel. At least some of the inflatable chambers may have at least one region at which the outer surface does not touch the inner wall of the blood vessel when the chamber is inflated, and these regions may advantageously be arranged at different angular locations around the periphery of different ones of the chambers In the above described methods, the cleaning element may comprise at least one flexible disc-shaped element attached to a body, the flexible disc-shaped element having an outer diameter at least as large as the internal diameter of the blood vessel of the subject in the region where the stenosis is expected. The clearing device may then further comprise threads attached to outer portions of the at least one flexible disc-shaped element, the method further comprising the step of applying tension to the threads such that the at least one flexible disc-shaped element can be stowed onto the body. In either case, at least one of the flexible disc-shaped elements may be constructed of a polymeric material.

In any of the above described methods, the needle may be one entry arm of a bifurcated needle, the method further comprising the step of flowing blood into the blood vessel through the other entry arm of the bifurcated needle, or the needle may be a single bore needle, the method further comprising the step of flowing blood into the blood vessel through a second single bore needle.

Yet other implementations may involve the step of enabling the elution of a stenosis retarding drug from the periphery of the cleaning element, at least during passage through the blood vessel.

BRIEF DESCRIPTION OF THE DRAWINGS

The presently claimed invention will be understood and appreciated more fully from the following detailed description, taken in conjunction with the drawings in which:

DETAILED DESCRIPTION

Figure 1:
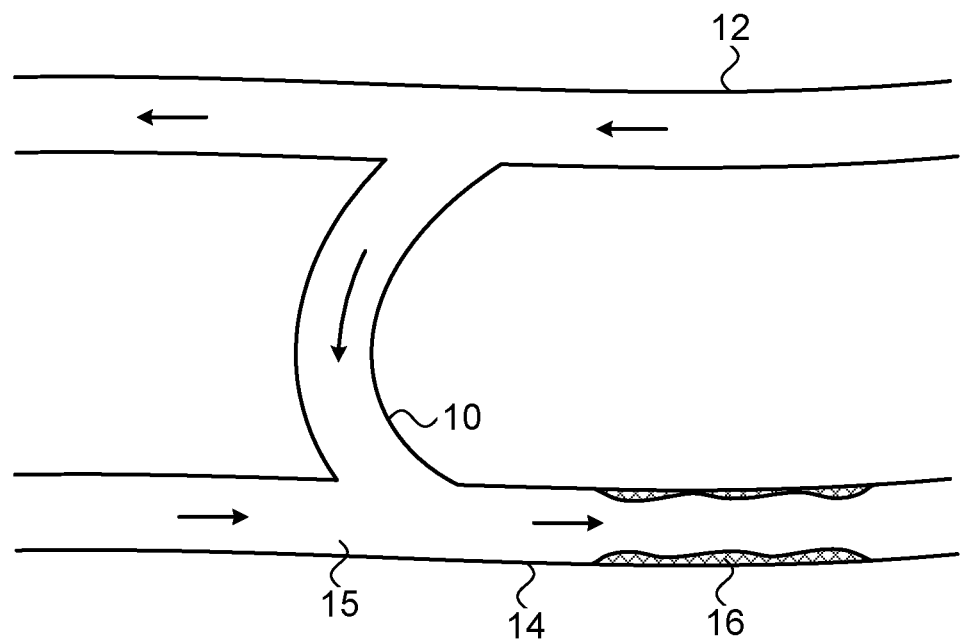
FIG. 1 illustrates schematically the layout of the vasculature in the forearm of a subject, with an arterial-venous shunt installed.

Reference is now made to FIG. 1, which illustrates schematically the layout of the vasculature in the forearm of the subject, with an arterial-venous shunt 10 installed between an artery 12 and a vein 14, as is customarily done for a subject undergoing a course of hemodialysis treatment. The arrows in the blood vessels and in the shunt show the direction of blood flow. The needle for withdrawing blood for sending to the dialysis machine can either be inserted into the shunt 10 itself, or into the vein immediately after the point at which the shunt joins the vein 15. In FIG. 1 there are shown a deposit of unwanted lesion tissue 16 in the vein, downstream from the shunt-vein joining point, resulting from stenosis of the vein supposedly associated with the presence of the dialysis shunt. In many cases, this plaque deposits extends for a distance of 1 to 2 cm from the shunt-vein junction 15.

Figure 2:
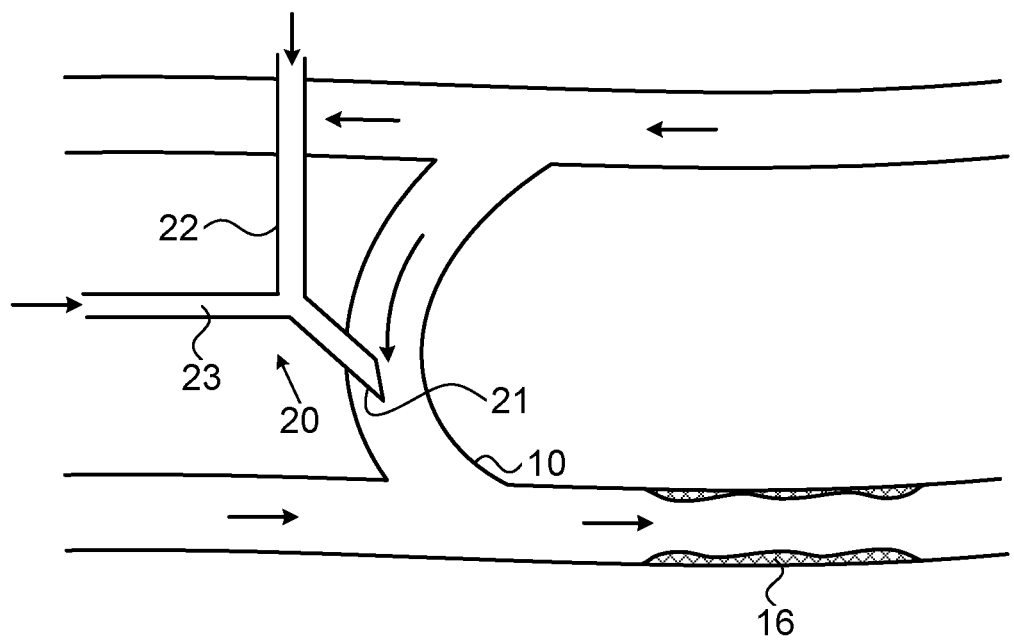
FIG. 2 shows schematically illustrates an exemplary system as disclosed in this application, for the prevention of shunt stenosis.

Reference is now made to FIG. 2, which illustrates schematically an exemplary kit for the prevention of shunt stenosis, as described in the present disclosure. The system comprises a Y-needle 20 having a needle cannula leg 21 with a sharp point for puncturing and inserting into a blood vessel, and two arms 22, 23 for input to the needle cannula leg. The Y-needle is adapted to be inserted into the shunt as shown in FIG. 2, though in certain cases it may be inserted into the vein close to the shunt junction. One free arm 22 of the Y-needle is used for attachment to the dialysis machine, for transferring cleaned blood from the machine to the patient. The other free arm 23 of the Y needle 20 is used for inserting the second component of the kit which is the cleaning device, to be shown in FIG. 3A or 3B and 4A or 4B, used for ensuring that no unwanted tissue growth 16 builds up within the vein, or for removing plaque that has already built up there. The cleaning device is sent through the arm 23 of the Y needle 20, through the needle cannula leg 21, into the shunt and from there into the vein where the stenosis tissue buildup exists, or where the potential buildup is expected. The cleaning device has a tether lead attached to its rear (proximal) end, so that it can be removed back through the Y needle arm once the cleaning procedure has been completed, by pulling on the tether lead. This action can be done either manually, or by means of an automated winch (not shown) to enable the system to be automated for use by non-technical personnel, such as the patient him/herself.

Figure 3A:
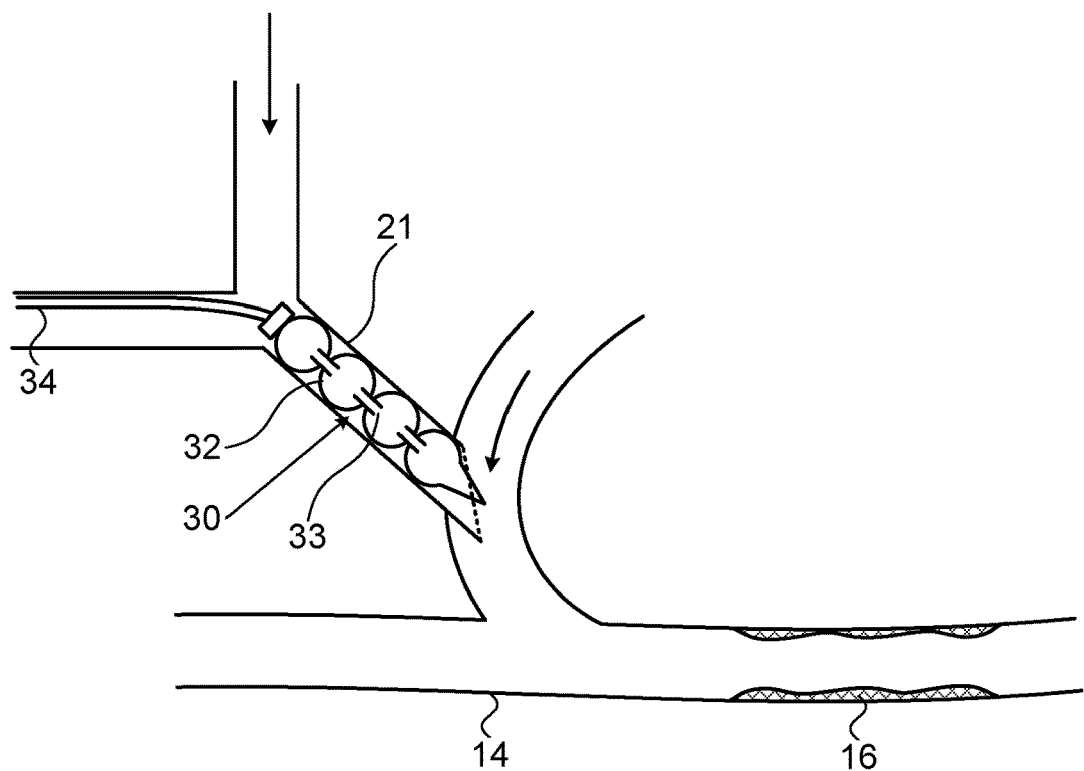
FIGS. 3A and 3B show schematically a first exemplary implementation of the cleaning device, in the form of a self-propelled locomotion device.
Figure 3B:
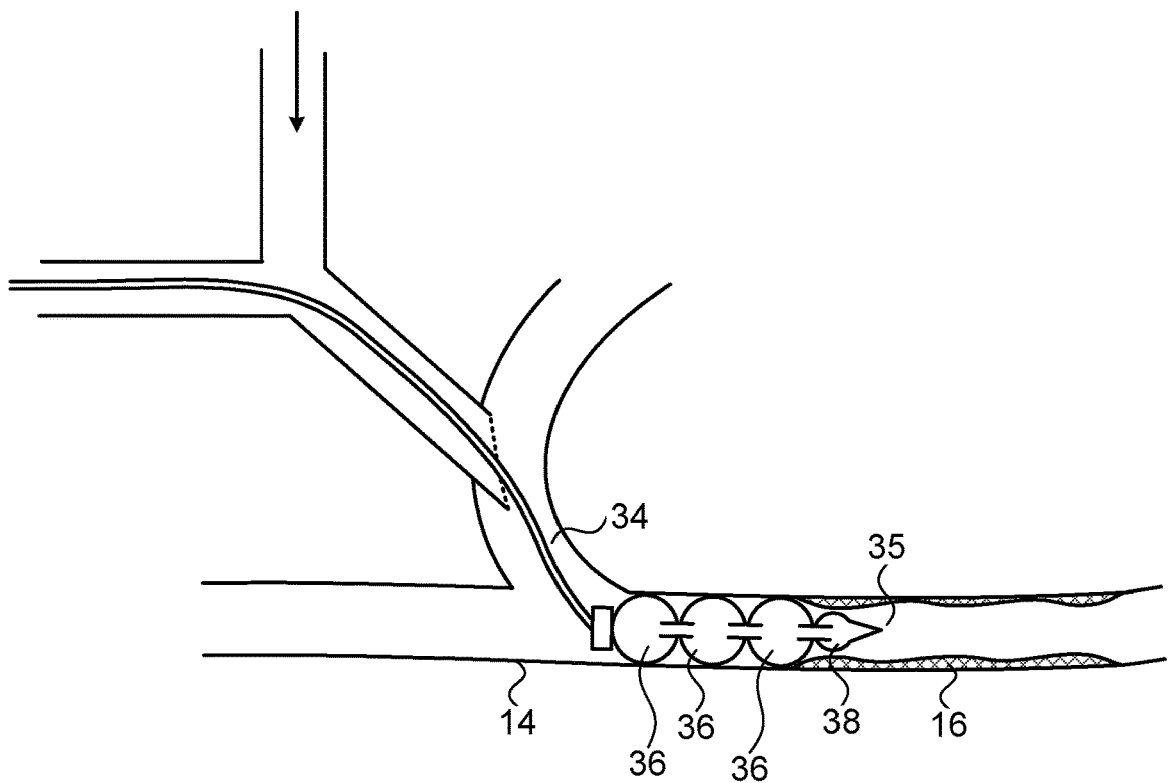

Reference is now made to FIGS. 3A and 3B, which show a first exemplary implementation of the cleaning device, in the form of a self-propelled locomotion device 30 for passage through the needle and blood vessels, using a series of sequentially inflating balloons 32 connected by passages 33 having a predetermined flow rate for the fluid. The device is powered by an inflation line 34 trailing out behind the device which causes the balloons to inflate sequentially. Such a device has been previously described in the above referenced WO 2007-017876 International Patent Publication, herewith incorporated by reference in its entirety. In FIG. 3A, there is shown how the cleaning device 30 in its non-inflated form, has a diameter sufficiently small that it can pass through the bore of the Y-needle to gain access to the blood vessel 14 to be treated. By this means, a Y-needle of acceptable diameter, significantly less than that of the shunt or the blood vessels, can be used.

FIG. 3B now shows schematically how, once the cleaning device 30 has traversed the Y-needle cannula leg 21, it can then be actuated by application of fluid pressure to the inflation line 34, resulting in sequential inflation of the balloons of the device, such that they expand and contact the inner walls of the shunt or blood vessel, which generally have an inner diameter substantially larger than that of the Y-needle, and in addition, move in the forward direction as the balloons expand axially as well as radially. In the example shown in FIG. 3B, three 36 of the four balloons have inflated, and the most distal one 38 is about to inflate. Although the blood flow may tend to sweep the cleaning device into the vein by virtue of its high flow rate, it is more advantageous that the device proceed by means of the sequential balloon inflating technology, such that the outer skin of the inflated balloons reach the inner walls of the blood vessel, and exert pressure on the plaque 16, forcing it against the inner wall of the vein. The pointed probe 35 at the front of the clearing device can assist in opening up a passage in the case of severe plaque accumulation. In cases where no plaque yet exists, which, if the device is used at sufficiently close intervals, should generally be the case, then the very passage of the inflated balloons along the inner walls of the vein should prevent growth of the plaque tissue at an early stage. Once the device has proceeded beyond the point at which the plaque needs to be cleared, it can be retracted from the vein by pulling backwards on the inflation line 34, or on a separate tether line (not shown) attached to the rear of the device. Before passage back through the Y-needle, the inflation pressure must be released so that the balloons deflate and the small diameter deflated device can be withdrawn through the Y-needle passages. If the withdrawal of the cleaning device up to the needle is performed with at least one of the balloons inflated, then the sliding passage of the inflated balloon or balloons on the inner wall of the blood vessel may enhance the cleaning process that was performed during the stage when the cleaning device was crawling forward in the blood vessel. Alternatively, the cleaning device can be caused to crawl forwards and be pulled backwards several times to increase the efficiency of the clearing process.

Figure 3C:
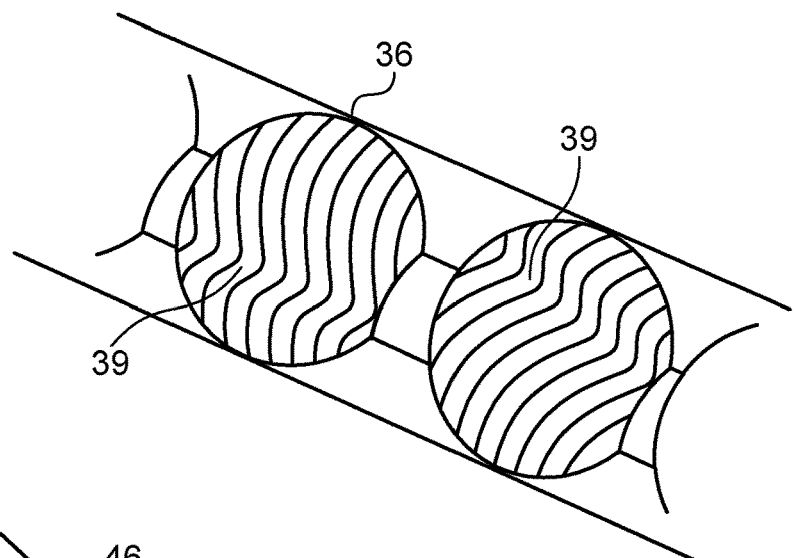
FIG. 3C is an isometric view of the implementation shown in FIG. 3B, showing offset circumferential blood by-pass passages in successive balloons.

Once the cleaning procedure has been completed, the cleaning device arm of the Y needle can be closed to prevent loss of blood, while dialysis continues through the other arm of the Y needle. In the isometric view of this implementation shown in FIG. 3C, circumferential blood by-pass passages 39 are shown in successive inflated balloons 36, to enable blood flow to continue even while the cleaning device is performing its function, with the outer surfaces of the balloon in contact with the inner walls of the blood vessel, except at the depressed by-pass channel regions 39. As shown in FIG. 3C, the passages may be disposed at different angular positions in different balloons such that the entire circumference of the inner wall of the blood vessel will be treated by pressure from one or other of the balloons.

Figure 4A:
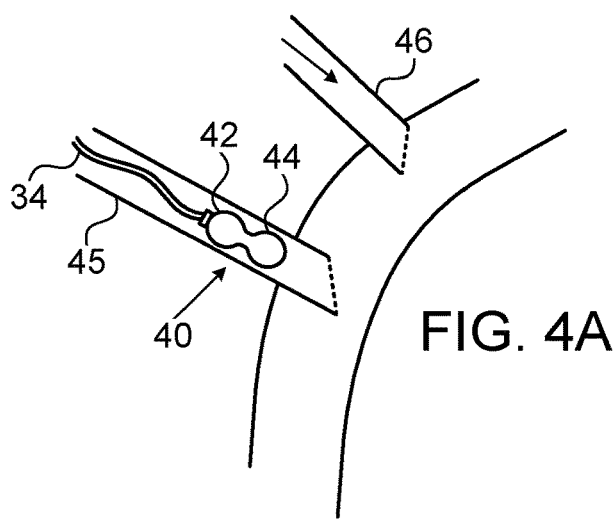
FIGS. 4A and 4B show schematically a second exemplary implementation of the cleaning device, using a single chamber balloon which is inflated from the trailing fluid inflation tube.
Figure 4B:
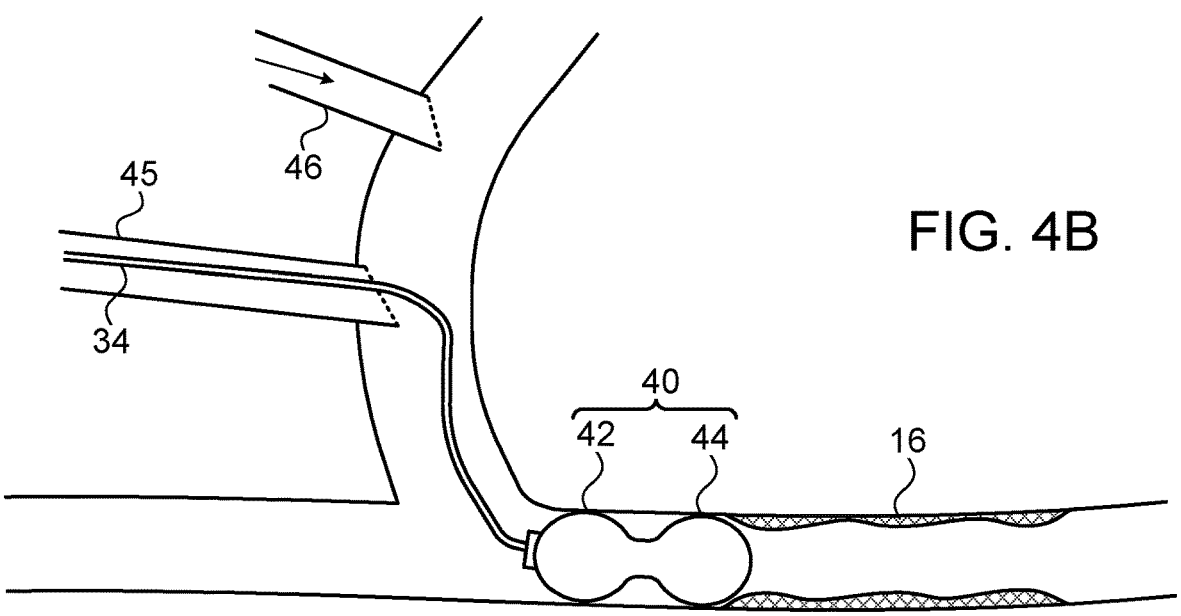

Reference is now made to FIGS. 4A and 4B, which show an alternative exemplary implementation of the cleaning device 40, comprising one or more inflatable balloons 42, 44. In FIGS. 4A and 4B, unlike the previous implementations of FIGS. 3A and 3B, the cleaning device 40 is illustrated being inserted into the shunt and vein by means of a single needle 45, instead of a Y-needle, while another single needle 46 is used for returning the blood after dialysis. This is an alternative to the use of a Y-needle, and is applicable also to any of the exemplary implementations shown in this disclosure. The extraction of blood to the dialysis machine is performed through another needle, not shown in FIGS. 3A and 3B. As in FIGS. 3A and 3B, FIG. 4A shows the cleaning device being inserted undeployed through the needle, while FIG. 4B shows the cleaning device in its deployed form after inflation within the blood vessel to be cleared.

However this implementation differs from that of FIGS. 3A and 3B in that the cleaning device is a passive device which relies on the blood flow for transporting it to the region of the vein which is to be kept free of obstruction. The cleaning device of FIGS. 4A and 4B may comprise a single balloon (this implementation not being shown in the drawings) which is inflated from the trailing fluid inflation tube 34, or a series of two or more balloons 42, 44, linked by openings sufficiently large that the balloons inflate essentially simultaneously, and may be considered as a single double chambered balloon. The advantage of using more than one balloon is that if a surface blood by-pass channel is used, as shown in FIG. 3C, then two successive balloons can have their channels positioned in different circumferential positions, to ensure that every region of the inner wall of the vein is treated. As shown in FIG. 4A, the cleaning device 40 is inserted through the arm of the needle 45 while it is in a deflated configuration. Once it is out of the needle bore and in the shunt or vein region, the balloons 42, 44, can be inflated by means of the fluid inflation tube 34, as shown in FIG. 4B and the inflation tube can be paid out to allow the inflated balloon device 40 to be swept downstream by the blood flow. It can then be pulled backwards and allowed to be swept forward over the region where plaque formation is to be found, or is expected to be formed, with or without repeated inflation and deflation in that region, thereby cleaning or maintaining the region free of obstruction. When the cleaning device is to be removed from the blood vessel, it is deflated, or even has suction applied to the inflation tube 34 to collapse the balloon or balloons completely such that they can withdrawn through the needle bore again.

Figure 5A:
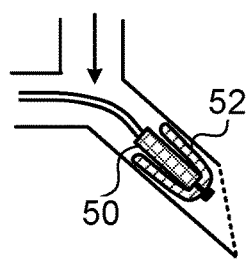
FIGS. 5A and 5B show schematically a further exemplary implementation of a blood flow transported cleaning device, using a flexible diaphragm disc to slide along the wall of the blood vessel.
Figure 5B:
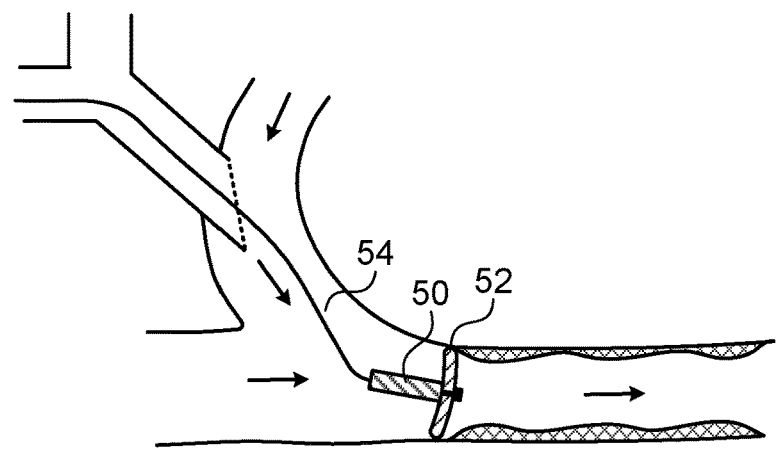

Another implementation which relies on the blood flow for transporting it to the region of the vein to be cleared is shown in FIGS. 5A and 5B. This implementation utilizes a cleaning device body 50 having one or more flexible flaps shaped in the form of discs 52 attached to the body 50, and which can slide against the inner wall of the blood vessel, ensuring that no stenotic tissue can grow there, and removing any which has already deposited there. As is shown in FIG. 5A, the cleaning device can advantageously be inserted through the Y-needle with the flexible discs 52 folded inwards and rearwards, such that they can traverse the comparatively small bore of the Y-needle. As now shown schematically in FIG. 5B, once through the Y-needle and in the wider diameter shunt or blood vessel, the flexible disc or discs 52 can open to their deployed size, making contact with the inner wall of the blood vessel. One advantageous implementation involves a circular disc structure, with the disc or discs of slightly larger diameter than the inner diameter of the blood vessel, such that they cannot open to a direction normal to the device axis, but form an umbrella or a parachute like structure. The inner volume formed by the angled discs are angled in the direction such that the flow of blood fills that volume and sweeps the device in the direction of the flow by filling the hollow disc structure and applying a hydraulic locomotive force to the cleaning device. The cleaning action itself may be more effective when the cleaning device is retracted in the reverse direction by means of its tether line 54, since during such a backward motion, the circular disc structure tends to be pushed open and to slide along the walls of the vein through which it is being pulled. The disc structure should be constructed of a sufficiently flexible and soft material, such as a pliable polymer material, such that it can fold up compactly when being inserted through the Y-needle or removed, and also so that it does not do any damage to the walls of the vein while it is sliding along the walls. Although the implementation of FIGS. 5A to 7B show only a single diaphragm disc attached to the body 50, it is to be understood that the invention can also be performed using a body with multiple serially disposed diaphragm discs on it.

As in the case of the inflated balloon implementation shown in FIGS. 3A and 3B, it may be advantageous to have openings made in the discs so that the blood flow can continue even when the cleaning device is operating in the vein. Because of the simpler structure of this implementation, the opening may be made anywhere in the disc, and advantageously away from the edges, such that the edges slide along the inner wall of the vein around the whole circumference of the disc. Alternatively a number of discs may be used each with a circumferential passageway angularly rotated relative to its neighboring discs, so that the cleaning efficiency is not reduced.

Figure 6:
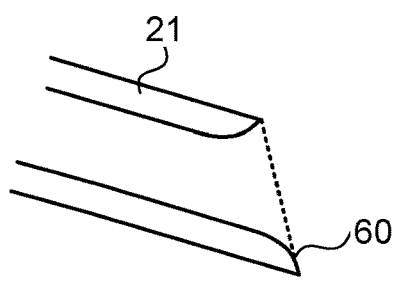
FIG. 6 shows an enlarged view of the insertion point of a Y-needle having a slightly rounded inner edge to assist in withdrawal of the cleaning device.
Figure 7A:
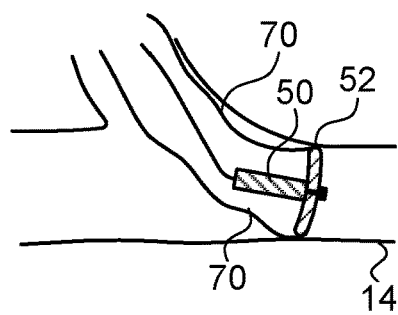
FIGS. 7A and 7B show an implementation of the cleaning device of FIGS. 5A and 5B, incorporating fine retraction threads attached to circumferential points of the discs to assist in withdrawal of the cleaning device.
Figure 7B:
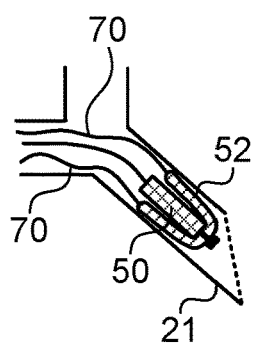

When withdrawing the device, once the pointed tip of the needle cannula leg 21 of the Y-needle is reached, the discs need to be folded inwards again in order to enter the smaller bore of the Y-needle. If the disc can be made sufficiently strong and sufficiently thick that the sharp edge of the needle point does not cut it off, then the cleaning device can simply be pulled back through the needle, and will fold over in the reverse direction to its deployed direction in the vein. A slightly rounded inner edge 60 to the insertion leg 21 of the needle may assist in this process, as shown in FIG. 6. Alternatively, as shown in FIG. 7A showing the cleaning device deployed in a vein 14, and FIG. 7B, showing the cleaning device stowed in the needle leg 21, fine retraction threads 70 could be attached to circumferential points of the discs, like parachute cords, in order to pull the circumferential lips of the discs inward to the size of the needle bore, so that the cleaning device can be stowed at a size sufficiently small for extraction through the needle.

In any of the above described implementations, the cleaning device can be equipped with a drug eluting component, designed to retard or even prevent the stenosis growth in the blood vessel. The drug elution may advantageously be performed from the peripheral regions of the cleaning device, so that the drug has intimate contact with any stenosis tissue growth along the walls of the blood vessel.

It is appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

We claim:

1. A system for reducing dialysis shunt stenosis in a blood vessel of a subject, the system comprising:
   at least one clearing device adapted to move autonomously within said blood vessel;
   a first needle bore configured to enable insertion therethrough of said at least one clearing device into said blood vessel; and
   a second needle bore configured to enable flow of dialyzed blood into said blood vessel;
   wherein said at least one clearing device is configured to be actuated from externally to the body of the subject.

2. A system according to claim 1, wherein said at least one clearing device is configured to allow continued flow of blood through said blood vessel when said at least one clearing device is disposed in said blood vessel.

3. A system according to claim 1, further comprising a tether attached to said at least one clearing device, said tether being configured to enable withdrawing of said at least one clearing device from said blood vessel.

4. A system according to claim 1, wherein said at least one clearing device is configured to contact the inner wall of said blood vessel as it moves therewithin.

5. A system according to claim 1, wherein said at least one clearing device comprises a locomotive system by means of which said at least one clearing device is configured to move along said blood vessel.

6. A system according to claim 1, wherein said at least one clearing device comprises at least one inflatable chamber whose inflated diameter is such that a periphery of said at least one inflatable chamber applies pressure to said inner wall of said blood vessel when said at least one inflatable a chamber is inflated.

7. A system according to claim 6, wherein said at least one inflatable chamber comprises a series of inflatable chambers, and wherein said series of said inflatable chambers is configured such that application of fluid pressure to the proximal chamber of said series of inflatable chambers causes the inflatable chambers to sequentially expand radially and axially.

8. A system according to claim 1, wherein said at least one clearing device comprises at least one flexible disc having an outer diameter at least as large as the internal diameter of said blood vessel in the region where said stenosis is expected.

9. A system according to claim 1, wherein said at least one clearing device includes a tapered tip configured to facilitate the clearing of blockages within said blood vessel.

10. A system according to claim 1, wherein said at least one clearing element is drug eluting, said drug being a stenosis retarding drug.

11. A system according to claim 1, wherein said first needle bore and said second needle bore are bores defined in one of: two arms of a bifurcated needle, two arms of a Y-junction connected to a single needle or two separate single bore needles.

12. A system for reducing dialysis shunt stenosis in a blood vessel of a subject, the system comprising:
at least one clearing device adapted to move autonomously within said blood vessel;
a first needle arm configured to enable insertion therethrough of said at least one clearing device into said blood vessel; and
a second needle arm configured to enable flow of dialyzed blood into said blood vessel;
wherein said at least one clearing device is configured to be actuated from externally to the body of the subject.

13. A system according to claim 12, wherein said first and second needle arms are two arms of a bifurcated needle.

14. A system according to claim 12, wherein said first and second needle arms are two arms of a Y-junction connected to a single needle.

15. A system according to claim 12, wherein said first and second needle arms are two separate single bore needles.

16. A system according to claim 12, wherein said at least one clearing device is configured to allow continued flow of blood through said blood vessel when said at least one clearing device is disposed in said blood vessel.

17. A system according to claim 12, further comprising a tether attached to said at least one clearing device, said tether being configured to enable withdrawing of said at least one clearing device from said blood vessel.

18. A system according to claim 12, wherein said at least one clearing device comprises a locomotive system by means of which said at least one clearing device is configured to move along said blood vessel.

19. A system for reducing dialysis shunt stenosis in a blood vessel of a subject, the system comprising:
at least one clearing device adapted to move autonomously within said blood vessel;
a first needle arm configured to enable insertion therethrough of said at least one clearing device into said blood vessel; and
a second needle arm configured to enable flow of dialyzed blood into said blood vessel;
wherein said at least one clearing device is configured to allow continued flow of blood through said blood vessel when said at least one clearing device is disposed in said blood vessel.

20. A system according to claim 19, wherein said at least one clearing device is configured to be actuated from externally to the body of the subject.

* * * * *